United States Patent [19]

Garthoff et al.

[11] Patent Number: 4,859,665
[45] Date of Patent: Aug. 22, 1989

[54] ANTIHYPERTENSIVE COMBINATION PRODUCTS CONTAINING A DIHYDROPYRIDINE AND A PYRIDAZODIAZEPINE

[75] Inventors: Bernward Garthoff, Hilden, Fed. Rep. of Germany; Marcel Gerold, Binningen; Fridolin Hefti, Allschwil, both of Switzerland; Stanislav Kazda, Wuppertal; Andreas Knorr, Erkrath, both of Fed. Rep. of Germany

[73] Assignees: Hoffmann-LaRoche Inc., Nutley, N.J.; Bayer Akt., Leverkusen, Fed. Rep. of Germany

[21] Appl. No.: 937,867

[22] Filed: Dec. 2, 1986

[30] Foreign Application Priority Data

Dec. 4, 1985 [DE] Fed. Rep. of Germany ....... 3542794

[51] Int. Cl.$^4$ ............... A61K 31/33; A61K 31/345; A61K 31/44; A61K 31/55
[52] U.S. Cl. ............... 514/221; 514/218; 514/247; 514/277; 514/354; 514/355; 514/356; 514/929
[58] Field of Search ............ 514/236, 253, 222, 356, 514/929, 218, 221, 247, 277, 355, 354, 338, 339, 361, 461, 469, 471; 544/250

[56] References Cited

U.S. PATENT DOCUMENTS

| | | | |
|---|---|---|---|
| 3,799,934 | 3/1974 | Meyer et al. | 546/257 |
| 3,932,645 | 1/1976 | Meyer et al. | 514/356 |
| 3,932,645 | 1/1976 | Meyer et al. | 514/356 |
| 4,504,476 | 3/1985 | Schwartz et al. | 514/211 |
| 4,512,924 | 4/1985 | Attwood et al. | 514/221 |
| 4,532,237 | 7/1985 | Hartman et al. | 514/236 |
| 4,599,341 | 7/1986 | Halczenko et al. | 514/236 |
| 4,656,188 | 4/1987 | Veber et al. | 514/221 |
| 4,703,038 | 10/1987 | Garthoff et al. | 514/356 |

FOREIGN PATENT DOCUMENTS

| | | |
|---|---|---|
| 2117571 | of 0000 | Fed. Rep. of Germany . |
| 3317290 | of 0000 | Fed. Rep. of Germany . |
| 2037766 | 7/1980 | United Kingdom ............ 514/356 |

OTHER PUBLICATIONS

Journal of Cardiovascular Pharmacology, 7, S 82–S 87, 1985, MacGregor et al.
Journal of Cardiovascular Pharmacology, 7, S 88–S 91, 1985, Browner et al.
Journal of Cardiovascular Pharmacology, 7, S 92–S 95, 1985, Mimran et al.
Goodman and Gilman's, "The Pharmacological Basic of Therapeutics", 6th Edition, (1980), pp. 808–814.
Sweet et al.; J. Cardiovascular Pharm., 8(Suppl. 1):S15–S19, (1986).

Primary Examiner—Ronald W. Griffin
Assistant Examiner—Nancy S. Carson
Attorney, Agent, or Firm—Jon S. Saxe; Bernard S. Leon; William G. Isgro

[57] ABSTRACT

Compositions for treating hypertension comprising an effective amount of a dihydropyridine of the formula

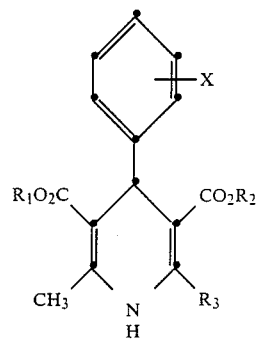

in which
X is 1 or 2 identical or different substituents from the group consisting of nitro, chlorine and trifluoromethyl, or together with the phenyl ring, the group (Abstract continued on next page.)

NITRENDIPINE (3 mg/kg PERORALLY), CILAZAPRIL (3 mg/kg PERORALLY)
AND CILAZAPRIL & NITRENDIPINE (IN EACH CASE 3 mg/kg PERORALLY)

• o • NITRENDIPINE
—△— CILAZAPRIL

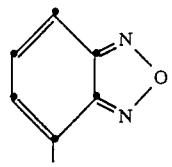

$R^1$ is alkyl of 1 to 4 C atoms, which is optionally substituted by alkoxy of 1 to 4 C atoms, $R^2$ is alkyl of 1 to 12 C atoms, which is optionally substituted by alkoxy of 1 to 3 C atoms, fluorine or N-methyl-N-benzylamino and $R^3$ is alkyl of 1 to 4 C atoms, cyano or hydroxymethyl, and a pyridazodiazepine of the formula

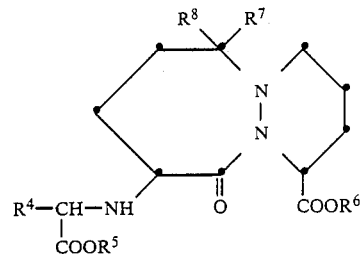

in which
$R^4$ is aralkyl,
$R^5$ is hydrogen or alkyl of 1 to 8 C atoms,
$R^6$ is hydrogen or alkyl of 1 to 8 C atoms and
$R^7$ and $R^8$ are hydrogen, or together, an oxo group, are described.

10 Claims, 6 Drawing Sheets

ANTIHYPERTENSIVE COMBINATION PRODUCTS CONTAINING A DIHYDROPYRIDINE AND A PYRIDAZODIAZEPINE

BRIEF SUMMARY OF THE INVENTION

The invention relates to pharmaceutical combination products for the treatment of hypertension, containing a dihydropyridine of the formula

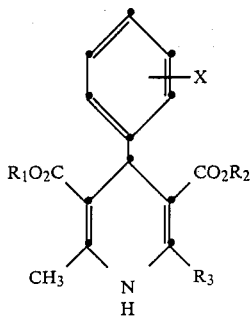

(I)

in which

X is 1 or 2 identical or different substituents from the group comprising nitro, chlorine and trifluoromethyl, or together with the Phenyl ring, the group

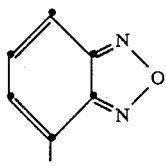

$R^1$ is alkyl of 1 to 4 C atoms, which is optionally substituted by alkoxy of 1 to 4 C atoms, $R^2$ is alkyl of 1 to 12 C atoms, which is optionally substituted by alkoxy of 1 to 3 C atoms, fluorine or N-methyl-N-benzylamino and $R^3$ is alkyl of 1 to 4 C atoms, cyano or hydroxymethyl, and a pyridazodiazepine of the formula

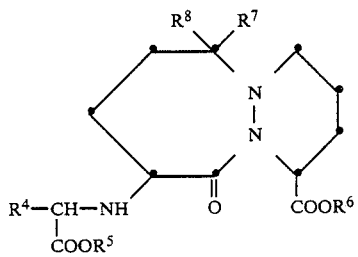

(II)

in which $R^4$ is aralkyl, $R^5$ is hydrogen or alkyl of 1 to 8 C atoms, $R^6$ is hydrogen or alkyl of 1 to 8 C atoms and $R^7$ and $R^8$ are hydrogen, or together, an an oxo group, the active compounds are present either in the form of their free bases or their hydrates or in the form of their pharmaceutically acceptable salts.

The pharmaceutical combination products of the invention are useful for the treatment of hypertension.

DETAILED DESCRIPTION OF THE INVENTION

Figure 1:
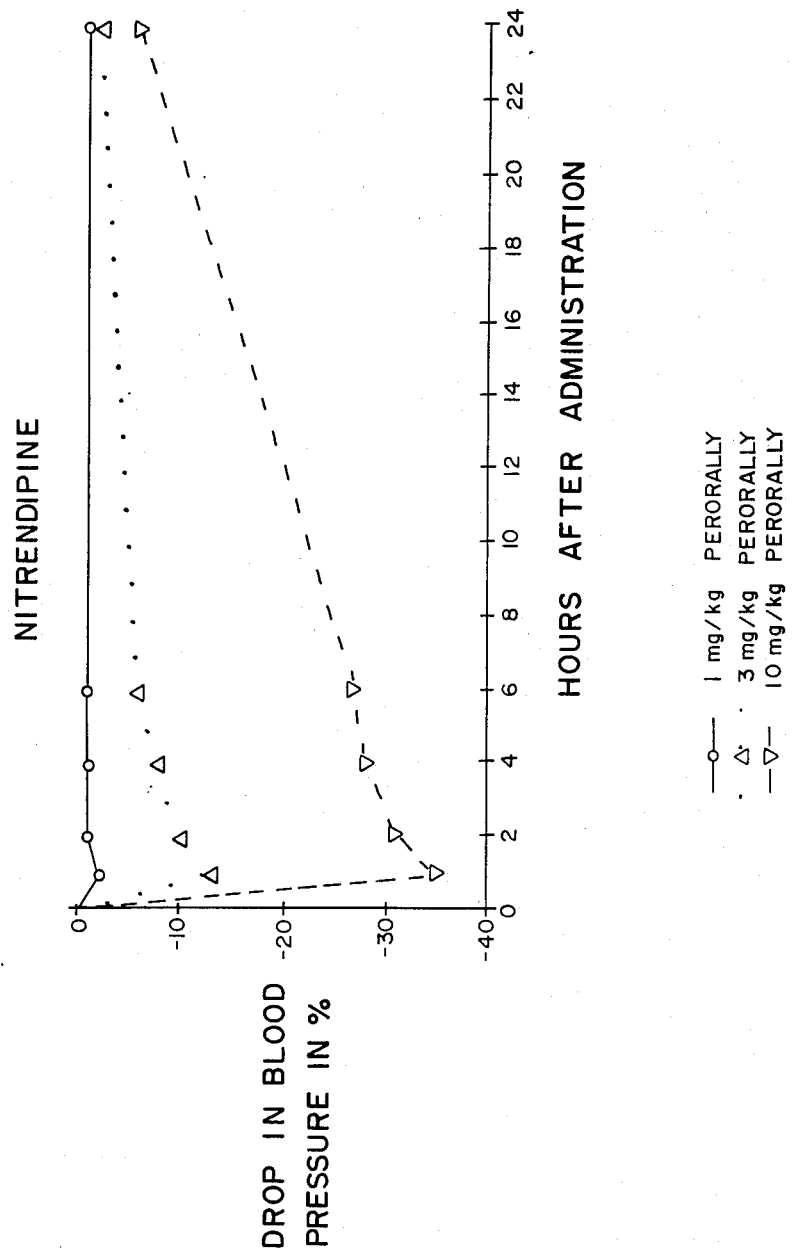

The invention relates to pharmaceutical combination products which are suitable for the treatment of hypertension and contain certain dihydropyridines and pyridazodiazepines.

The dihydropyridines mentioned are known calcium antagonists. They exhibit, inter alia, a pronounced antihypertensive action and can be used in the treatment of hypertension of all degrees of severity (see DE-OS (German Published Specification) No. 2,117,571) wherein the dihydropyridines under consideration are disclosed.

The pyridazodiazepines are known ACE inhibitors and are accordingly suitable for the treatment of hypertension. They exhibit hypotensive action without increasing the heart rate (see DE-OS (German Published Specification) No. 3,317,290) wherein the pyridazodiazepines under consideration are disclosed.

Combating hypertension with simultaneous administration of the hypotensive dihydropyridine 3-methyl 5-ethyl 2,6-dimethyl-4-(3-nitrophenyl)-1,4-dihydropyridine -3,5-dicarboxylate (hereinafter called nitrendipine) and the ACE inhibitor captopril has also been described (Journal of Cardiovascular Pharmacology. 7, pages 88 to 91 (1985)). The experiments described in the publication show that the patients treated with nitrendipine and captopril responded better, if at all. to simultaneous administration of both active compounds than to sole administration of nitrendipine or captopril, the two individual components having been used in these experiments in the doses required for the particular monotherapy.

There is a need to provide a pharmaceutical combination, administration of which leads to a reduction in blood pressure without simultaneously increasing the heart rate, and in which the doses of the individual components can be significantly reduced and undesirable side effects which occur in each case at the required dosage in monotherapy can be suppressed.

In the context of the invention, it was found that, on administration of the combination of a dihydropyridine with a pyridazodiazepine, in accordance with the invention, the hypotensive properties of the two individual components are not only added but, surprisingly, are potentiated (or synergized), which means that the effective doses of the two individual components can be reduced significantly. Moreover, it was not to be predicted that the duration of the action would at the same time be increased.

The antihypertensive combination according to the invention has the following advantages:

(a) the therapeutic amounts of each of the active compound to be administered are significantly reduced;

(b) undesirable side effects are eliminated or greatly reduced;

(c) the heart rate is not influenced or is influenced to the extent that there is a slight reduction;

(d) the duration of action is increased and (e) a uniform course of action is achieved.

The invention relates to pharmaceutical combination products for the treatment of hypertension. containing a dihydropyridine of the formula

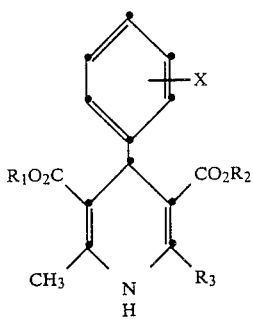

in which

X is 1 or 2 identical or different substituents from the group comprising nitro, chlorine and trifluoromethyl, or together with the phenyl ring, the group

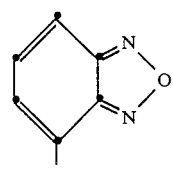

$R^1$ is alkyl of 1 to 4 C atoms, which is optionally substituted by alkoxy of 1 to 4 C atoms, $R^2$ is alkyl of 1 to 12 C atoms, which is optionally substituted by alkoxy of 1 to 3 C atoms, fluorine or N-methyl-N-benzylamino and $R^3$ is alkyl of 1 to 4 C atoms, cyano or hydroxymethyl, and a pyridazodiazepine of the formula

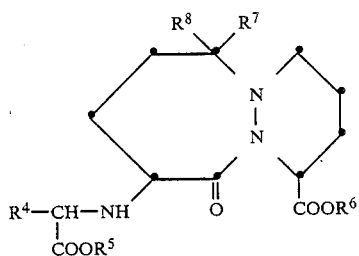

in which $R^4$ is aralkyl, $R^5$ is hydrogen or alkyl of 1 to 8 C atoms, $R^6$ is hydrogen or alkyl of 1 to 8 C atoms and $R^7$ and $R^8$ are hydrogen, or together, an oxo group the active compounds are present either in the form of their free bases or their hydrates or in the form of their pharmaceutically acceptable salts.

As used herein, the letter "C" denotes a carbon.

The aryl radical in aralkyl is the phenyl group, which can be mono- or polysubstituted by halogen, that is, fluorine, chlorine, bromine or iodine, alkyl of 1 to 8 C atoms, alkoxy of 1 to 8 C atoms, trifluoromethyl, phenyl and the like. The alkyl radical in aralkyl has 1 to 8 C atoms. Examples of aralkyl groups are benzyl, 4-chlorobenzyl, 2-phenylethyl, 3-phenylpropyl, 3-(4-(chlorophenyl)propyl, 3-(4-methoxyphenyl)propyl, 4-phenylbutyl and the like.

The salts of the active compounds include those formed with inorganic acids, for example. the hydrochloride, the hydrobromide or the like.

The weight ratio of the dihydropyridine to the pyridazodiazepine is advantageously about 10:1 to 1:10, preferably 8:1 to 1:8, based on the free base(s).

A weight ratio of 6-1 parts by weight of a dihydropyridine and 1-4 parts by weight of a pyridazodiazepine is particularly preferred. The daily dose to be administered by means of the combination is advantageously 5 to 20 mg of a dihydropyridine and 1 to 5 mg of a pyridazodiazepine. In general, the total amount of a dihydropyridine and a pyridazodiazepine to be administered daily is not more than 250 mg. If a hydrate or a pharmaceutically acceptable salt is used, the above values are to be changed accordingly.

The present invention thus relates to:

a combination of a dihydropyridine and a pyridazodiazepine, a pharmaceutical formulation containing a dihydropyridine and a pyridazodiazepine, the preparation of a pharmaceutical formulation, which is characterized in that a mixture of a dihydropyridine and a pyridazodiazepine is brought into a galenical presentation form, and the use of a combination of a dihydropyridine and a pyridazodiazepine or of a pharmaceutical formulation containing a dihydropyridine and a pyridazodiazepine for combating or preventing diseases, in particular circulatory diseases, and especially in combating or preventing hypertension and secondary diseases thereof without increasing the heart rate.

particularly suitable dihydropyridines are those of the formula I in which X is nitro or trifluoromethyl or 2 chlorine atoms, or together with the phenyl ring. the group

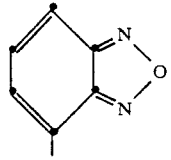

$R^1$ is alkyl of 1 to 4 C atoms, which is optionally substituted by methoxy, $R^2$ is alkyl of 1 to 12 C atoms, which is optionally substituted by methoxy or by 1 to 5 fluorine atoms, and $R^3$ is methyl, ethyl, cyano or hydroxymethyl.

Especially suitable dihydropyridines are those of the formula I in which X is nitro, $R^1$ and $R^2$ are identical or different and each is alkyl which is optionally substituted by methoxy and $R^3$ is methyl.

The most suitable representative from the group of dihydropyridines of the formula I is nitrendipine.

particularly suitable pyridazodiazepines are those of the formula II in which $R^4$ is aralkyl, $R^5$ is alkyl of 1 to 8 C atoms, $R^6$ is hydrogen and $R^7$ and R8 are hydrogen, or together, an oxo group.

Especially suitable pyridazodiazepines are those of the formula II in which $R^4$ is phenylalkyl, $R^5$ is alkyl of 1 to 4 C atoms and $R^6$, $R^7$ and $R^8$ are hydrogen.

The most suitable representative of the group of pyridazodiazepines of the formula II is 9(S)-[1(S)-ethoxycarbonyl-3-phenylpropylamino]octahydro-10-oxo -6H-pyridazo[1,2-a][1,2]diazepine-1(S)-carboxylic acid (hereinafter called cilazapril).

Advantageously, nitrendipine is present as the free base, while cilazapril is present as a pharmaceutically acceptable salt or hydrate. The combination as a rule contains cilazapril in the form of the corresponding hydrate or hydrobromide.

A preferred unit dose of a composition of the invention comprises 1 part of cilazapril and 8 parts of nitrendipine, or of, preferably, 1.25 mg and 10 mg, respectively.

A regular and long-lasting reduction in blood pressure without an increase in heart rate, coupled with a simultaneous good tolerance and low toxicity, can be achieved with small doses of active components with the combinations according to the invention.

The advantageous superadditive (or synergistic) hypotensive action of the combinations according to the invention in comparison with that of the two individual components can be demonstrated with the test procedures described below.

In a first experimental design, the hypotensive action on conscious, spontaneously hypertensive rats of the male sex weighing 280 to 320 g is determined. The systolic blood pressure and the heart rate are measured twice before administration of the substance. The substance is administered in repeated individual daily doses for 4 days. The two parameters are measured 1, 3, 6 and 24 hours after the administration. The systolic blood pressure is measured indirectly on the tail artery of the rat in accordance with the method of Gerold et al. (Arzneimittelforschung 18, 1285-1287, 1969). The following table summarizes the results obtained, which have been calculated as mean values from 5 experiments.

mg/kg of cilazapril has virtually no effect on peripheral resistance and shows only a very small hypotensive effect, and a dose of 0.1 mg/kg of nitrendipine shows only a short-term drop in blood pressure. In contrast, the action of a combination of 0.025 mg/kg of cilazapril and 0.1 mg/kg of nitrendipine is more potent than the sum of the two indiVidual substances and shows an essentially increased duration of action in comparison to nitrendipine alone. Analog results were also found in conscious dogs, cf. FIG. 6 which shows the hypotensive effect following oral administration of 2.5 mg/kg of cilazepril, 10 mg/kg of nitrendipine, and respectively, 12.5 mg/kg of a 1:4 combination of cilazapril and nitrendipine.

These results show the unexpectedly advantageous properties of the combinations according to the invention. From knowledge of the state of the art, it was not to be expected that precisely the combination of dihydropyridines, in particular nitrendipine, with pyridazodiazepines, in particular cilazapril, would show such a superior hypotensive action. Already knwn combinations of dihydropyridines with other ACE inhibitors display distinct disadvantages in comparison with the combinations according to the invention in respect of one or more properties, such as, for example, change in heart rate, duration of action or dosage required.

The combinations according to the invention are in general administered orally, for example in the form of tablets, lacquered or coated tablets, dragees, hard and soft gelatin capsules, solutions, emulsions or suspen-

| | Treatment | | | | | |
|---|---|---|---|---|---|---|
| Product | mg/kg per-orally 1 ×/day | duration (days) | Parameters | Control | Treated[1] | Number of test animals |
| Nitrendipine | 10 | 4 | SAP | 217.6 ± 1.1 | 222.0 ± 7.2 | |
| | | | HR | 443.0 ± 8.6 | 382.0 ± 11.6* | 5 |
| Cilazapril | 3 | 4 | SAP | 208.2 ± 3.1 | 196.0 ± 4.8 | 5 |
| | | | HR | 447.0 ± 10.8 | 426.0 ± 17.4 | |
| Nitrendipine + | 10 + | 4 | SAP | 200.6 ± 1.7 | 169.0 ± 2.9* | 5 |
| Cilazapril | 3 | | HR | 467.0 ± 12.5 | 358.0 ± 15.3* | |

[1]Measurement taken 24 hours after last administration
*Value significantly different (p < 0.5) from the control
SAP = Systolic arterial blood pressure (mm Hg)
HR = Heart rate (beats/min)

Figure 2:
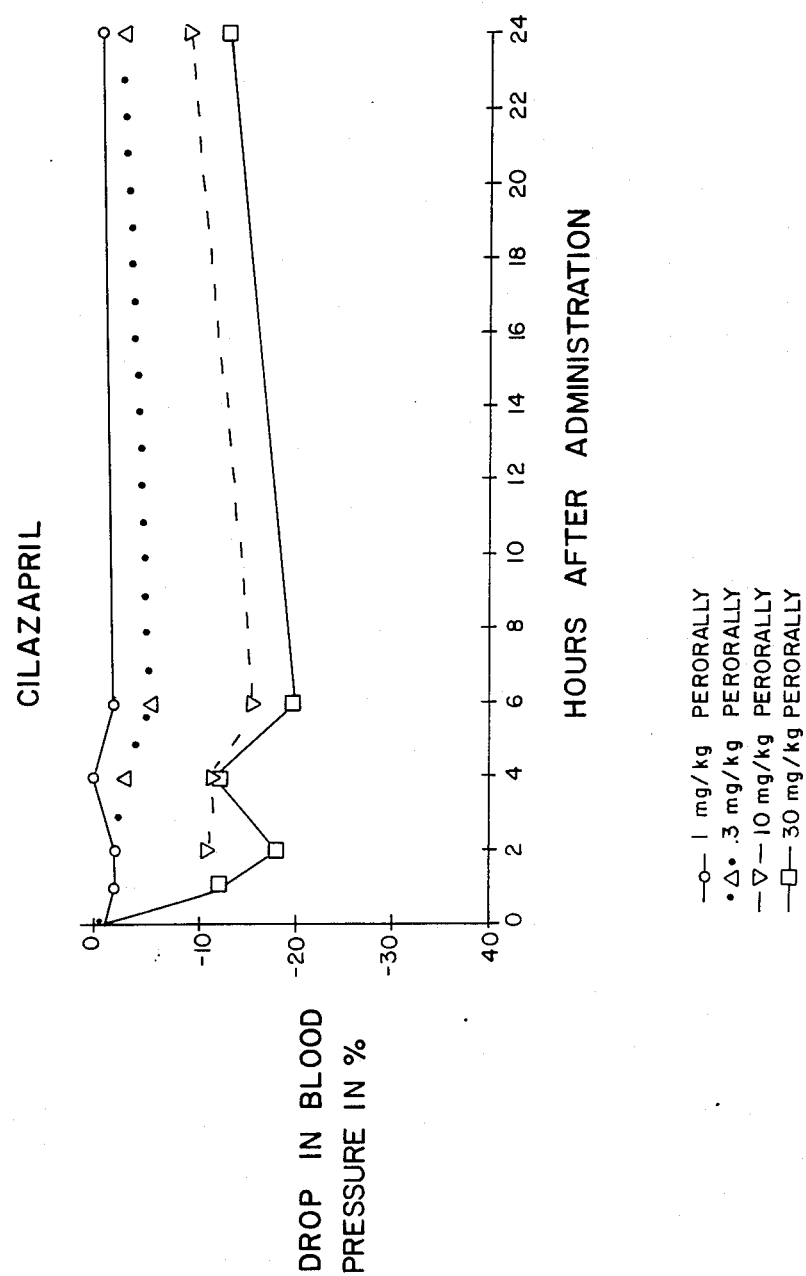
Figure 3:
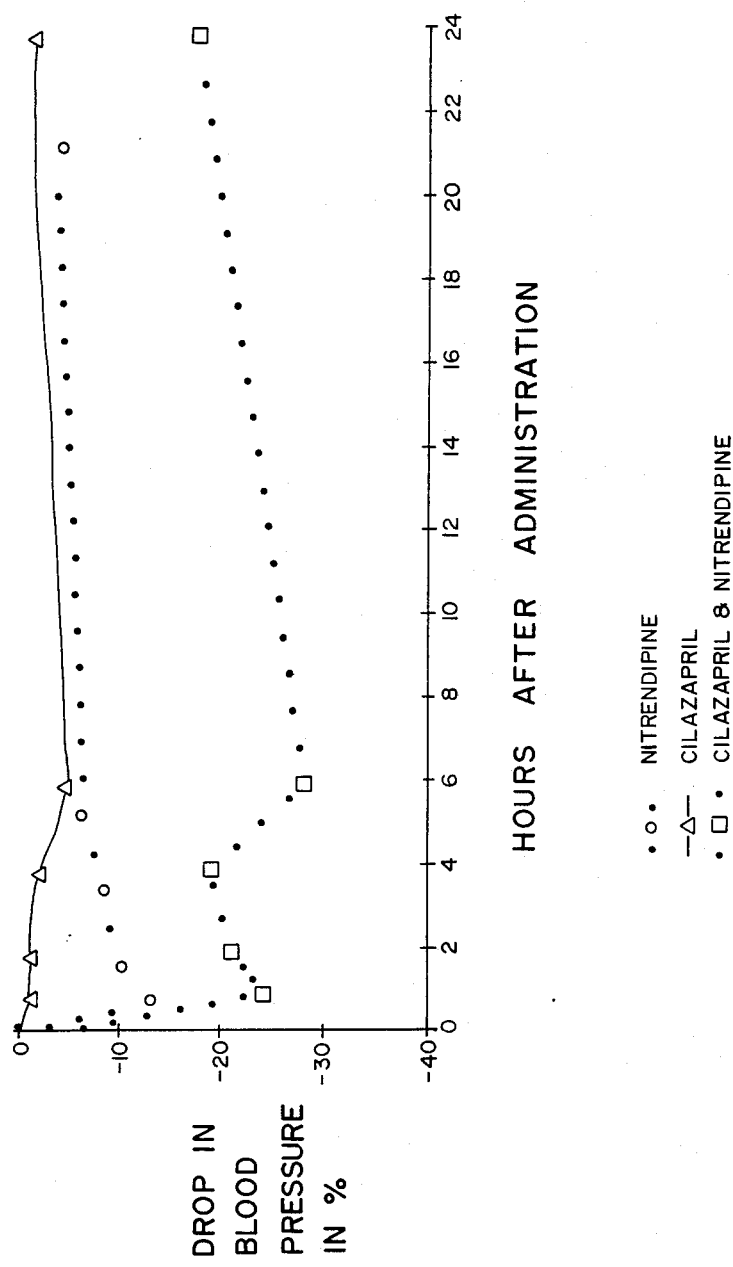

FIGS. 1 to 3 also document the superadditive (or synergistic) action of the combination according to the invention.

The hypotensive effect on hypertensive rats following oral administration of the individual substances nitrendipine and cilazapril independently can be seen in each case from FIGS. 1 and 2. A dose of 3 mg/kg of cilazapril has virtually no effect, and a dose of 3 mg/kg of nitrendipine shows only a very small and relatively short-term drop in blood pressure. In contrast, the action of a combination of 3 mg/kg each of nitrendipine and cilazapril is already more potent on oral administration than that of a ten times higher dose of cilazapril by itself, and it has a longer duration of action than a three times higher dose of nitrendipine by itself (see FIG. 3).

Furthermore, the superadditive (or synergistic) action and increased duration of action of the combination according to the invention can also be seen from FIGS. 4 to 6 below.

Figure 4:
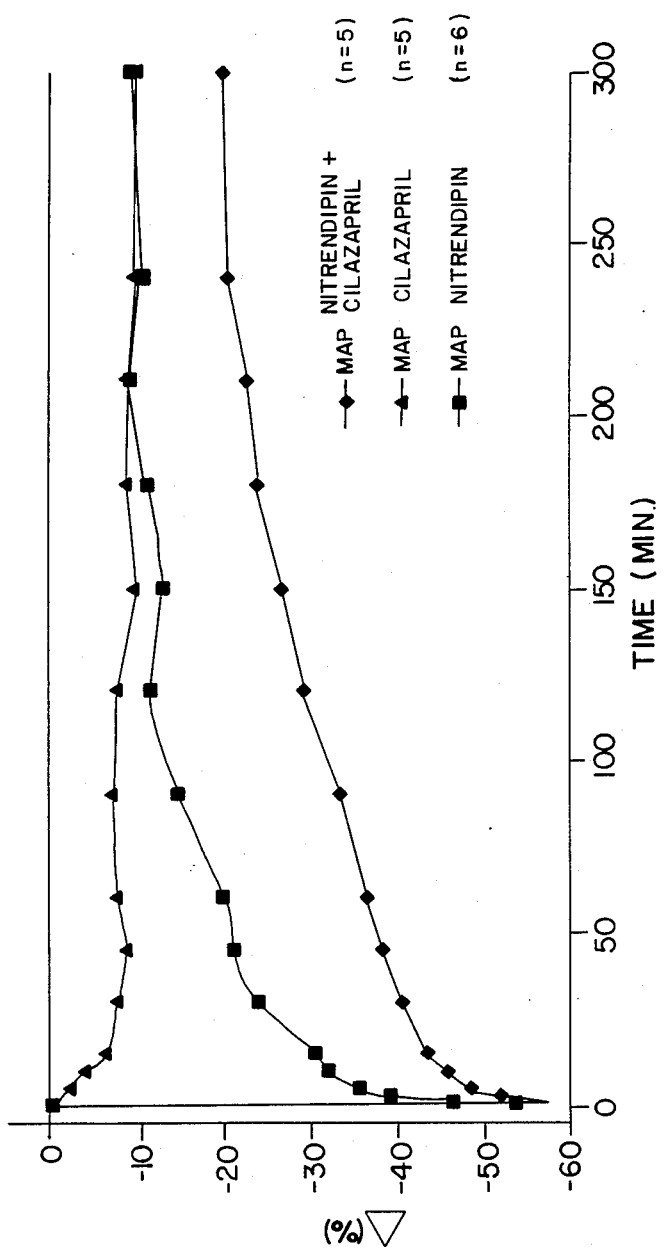
Figure 5:
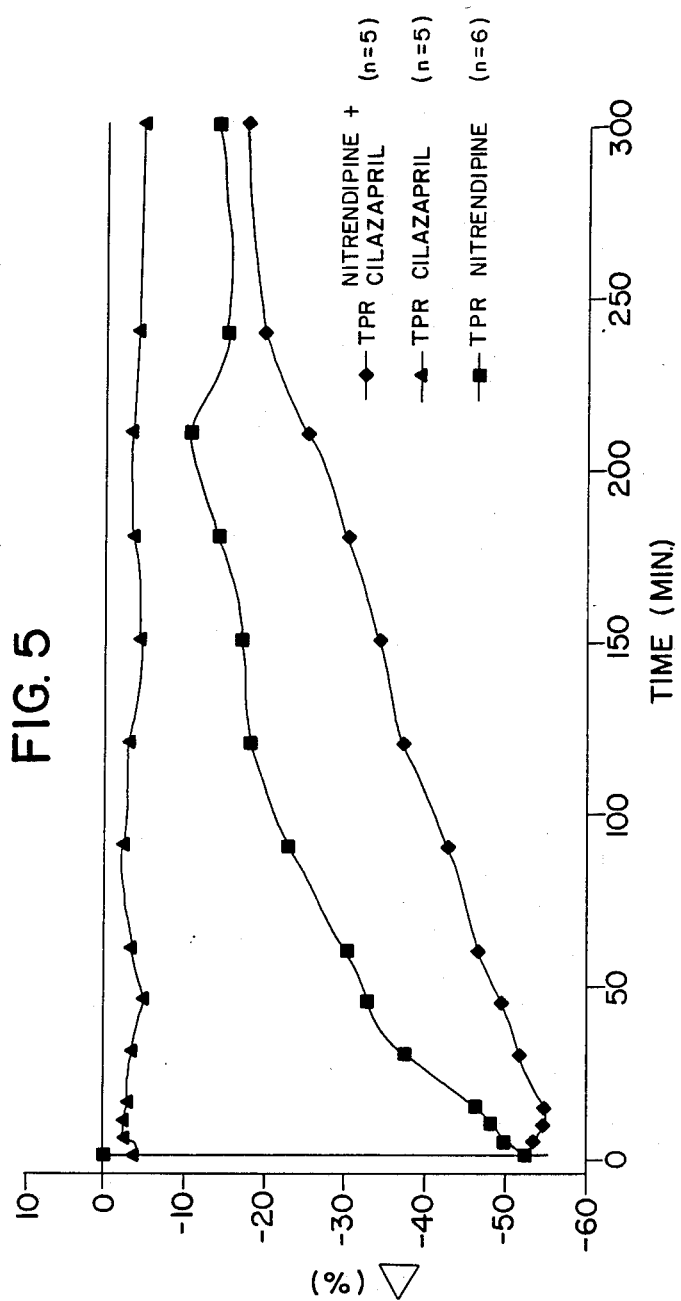
Figure 6:
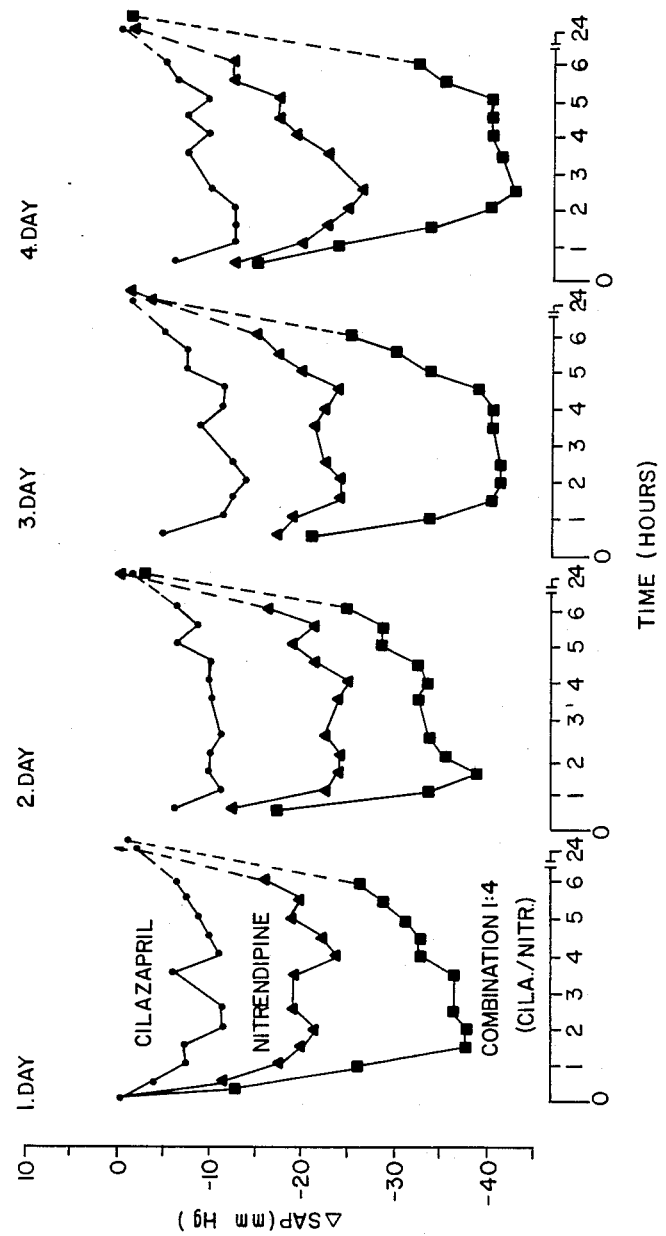

FIGS. 4 and 5 show the effects of the individual substancescilazapril and nitrendipine as well as of a combination thereof on mean arterial pressure and total peripheral resistance, respectively, in anaesthetized dogs after intravenous administration. A dose of 0.025 sions. However, they can also be administered rectally, for example in the form of suppositories, or parenterally, for example in the form of injection solutions.

To prepare tablets, lacquered or coated tablets, dragees and hard gelatin capsules, a combination according to the invention can be processed with pharmaceutically inert, inorganic or organic excipients. Excipients of this type which can be used for tablets, dragees and hard gelatin capsules, are, for example, lactose, corn starch or derivatives thereof, talc, stearic acid or salts thereof and the like.

Suitable excipients for soft gelatin capsules are, for example, vegetable oils, waxes, fats, semi-solid and liquid polyols and the like; depending on the nature of the active compound, however, no excipients at all are necessary with soft gelatin capsules.

Suitable excipients for the preparation of solutions and syrups are, for example, water, polyols, sucrose, invert sugar, glucose and the like.

Suitable excipients for injection solutions are, for example, water, alcohols, polyols, glycerol, vegetable oils and the like.

Suitable excipients for suppositories are, for example, natural or hardened oils, waxes, fats, semi-liquid or liquid polyols and the like.

The pharmaceutical formulations can additionally contain preservatives, solubilizing agents, stabilizers, wetting agents, emulsifiers, sweeteners, colorants, aromatizing agents, salts for modifying the osmotic pressure, buffers, coating agents or antioxidants. They can moreover also contain other therapeutically useful substances.

The following examples further illustrate the invention.

EXAMPLE 1

Preparation of hard gelatin capsules of the following composition:

| | |
|---|---|
| cilazapril | 2.5 mg |
| finely ground nitrendipine | 20.0 mg |
| powdered lactose | 17.5 mg |
| crystalline lactose | 70.0 mg |
| white corn starch | 20.0 mg |
| talc | 9.0 mg |
| magnesium stearate | 1.0 mg |
| total | 140.0 mg |

Method of Preparation

The active compounds are intensively mixed with the powdered lactose. This mixture is mixed with the crystalline lactose, white corn starch, talc and magnesium stearate. Size 4 capsules are filled with the powder.

EXAMPLE 2

Preparation of tablets of the following composition:

| | |
|---|---|
| cilazapril | 10.0 mg |
| finely ground nitrendipine | 2.5 mg |
| powdered lactose | 100.0 mg |
| white corn starch | 63.5 mg |
| polyvinylpyrrolidone | 4.0 mg |
| white corn starch | 15.0 mg |
| talc | 3.0 mg |
| magnesium stearate | 2.0 mg |
| total | 200.0 mg |

Method of Preparation

The active compounds are mixed with the powdered lactose and white corn starch. The mixture is moistened with an aqueous solution of the polyvinylpyrrolidone (PVP) and kneaded; the resulting mass is granulated and the granules are dried and sieved. The granules are mixed with white corn starch (2nd portion), talc and magnesium stearate and pressed into tablets of suitable size.

It will be understood that the specification and examples are illustrative but not limitative of the present invention and that other embodiments within the spirit and scope of the invention will suggest themselves to those skilled in the art.

What is claimed is:

1. A composition for combating hypertension comprising an effective amount of a dihydropyridine of the formula 3-methyl-5-ethyl-2,6-dimethyl-4-(3-nitrophenyl)-1,4-dihydropyridine-3,5-dicarboxylate and a pyriazodiazepine of the formula 9(S)-[1(S)-ethoxycarbonyl-3-phenyl-propylamino]octahydro-10-oxo-6H-pyridazo[1,2-a][1,2]diazepine-1(S)-carboxylic acid, wherein the weight ratio of the dihydropyridine to the pyridazodiazepine is from 10:1 to 1:10, and an inert carrier.

2. A composition according to claim 1, wherein the weight ratio of the dihydropyridine to the pyridazodiazepine is from 8:1 to 1:8.

3. A composition according to claim 2, wherein the 9(S)-[1(S)-ethoxycarbonyl-3-phenylpropylamino]octahydro-10-oxo-6H-pyridazo[1,2-a][1,2]diazepine-1(S)-carboxylic acid is a salt or hydrate.

4. A composition according to claim 2, wherein the 9(S)-[1(S)-ethoxycarbonyl-3-phenylpropylamino]octahydro-10-oxo-6H-pyridazo[1,2-a][1,2]diazepine-1(S)-carboxylic acid is a hydrobromide or hydrate.

5. A composition according to claim 1, wherein the weight ratio of the dihydropyridine to the pyridazodiazepine is from 6:1 to 1:4.

6. A unit dose of a composition according to claim 5, which contains 1 part of 9(S)-[1(S)-ethoxycarbonyl-3-phenylpropylamino]octahydro-10-oxo-6H-pyridazo[1,2-a][1,2]-diazepine-1(S)-carboxylic acid and 4 parts of 3-methyl-5-ethyl 2,6-dimethyl-4-(3-nitrophenyl)-1,4-dihydropyridine-3,5-dicarboxylate.

7. A unit dose of a composition according to claim 1, in which from 5 to 20 mg of the dihydropyridine and 1 to 5 mg of the pyridazodiazepine are present.

8. A unit dose of a composition according to claim 1, wherein the total weight of the dihydropyridine and the pyridazodiazepine is not more than 25 mg.

9. A method of reducing blood pressure in a host requiring such treatment which comprises administering to such a host an effective amount of a composition which comprises a pyridazodiazepine having the formula 9(S)-[1(S)-ethoxycarbonyl-3-phenyl-propylamino]octahydro-10-oxo-6H-pyridazo[1,2-a][1,2]diazepine-1(S)-carboxylic acid and a dihydropyridine having the formula 3-methyl-5-ethyl 2,6-dimethyl-4-(3-nitrophenyl)-1,4-dihydropyridine-3,5-dicarboxylate, wherein the weight ratio of the dihydropyridine to the pyridazodiazepine is from 6:1 to 1:4, and an inert carrier.

10. A method according to claim 9, wherein the composition comprises 1 part of 9(S)-[1(S)-ethoxycarbonyl-3-phenylpropyl-amino]octahydro-10-oxo-6H-pyridazo[1,2-a][1,2]-diazepine-1(S)-carboxylic acid and 4 parts of 3-methyl-5-ethyl 2,6-dimethyl-4-(3-nitrophenyl)-1,4-dihydropyridine-3,5-dicarboxylate.

* * * * *